US00PP28849P3

(12) United States Plant Patent
Menzel

(10) Patent No.: US PP28,849 P3
(45) Date of Patent: Jan. 2, 2018

(54) ***MISCANTHUS* PLANT NAMED 'LITTLE MISS'**

(50) Latin Name: *Miscanthus sinensis*
Varietal Denomination: Little Miss

(71) Applicant: Klaus Menzel, Woellstein (DE)

(72) Inventor: Klaus Menzel, Woellstein (DE)

( * ) Notice: Subject to any disclaimer, the term of this patent is extended or adjusted under 35 U.S.C. 154(b) by 0 days.

(21) Appl. No.: 14/999,034

(22) Filed: Mar. 22, 2016

(65) Prior Publication Data

US 2017/0280609 P1 Sep. 28, 2017

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Keith O Robinson
(74) *Attorney, Agent, or Firm* — Bethany R. Roahrig; Barbara Campbell; Cochran Freund & Young, LLC

(57) ABSTRACT

A new and distinct cultivar of *Miscanthus* plant named 'Little Miss' that is characterized by compact mounding habit, short height, green foliage becoming red early in the season and turning to dark burgundy red by fall. In combination, these traits set 'Little Miss' apart from all other existing varieties of *Miscanthus* known to the inventor.

3 Drawing Sheets

Genus and species: *Miscanthus sinensis.*
Variety denomination: 'Little Miss'.

BACKGROUND OF THE NEW PLANT

The present invention relates to a new and distinct cultivar of *Miscanthus*, also known as Maiden Grass, which is grown as an ornamental plant for use in the garden and landscape. The new cultivar is known botanically as *Miscanthus sinensis* and will be referred to hereinafter by the cultivar name 'Little Miss'. The genus *Miscanthus* is included in the plant family Poaceae.

'Little Miss' was discovered in 2004 as an open-pollinated seedling which was growing in the inventor's garden in Woellstein, Germany. The inventor has a particular interest in the genus *Miscanthus* and had assembled in his garden unnamed seedlings and the following named varieties (all unpatented) of *Miscanthus sinensis*: 'Adagio', 'Ferner Osten', 'Ghana', 'Kleine Fontane', 'Kleine Silberspinne', and 'Roter Pfeil'.

The inventor observed that the new variety 'Little Miss' was exceptionally low-growing in comparison with other *Miscanthus* varieties known to the inventor. The plant habit of 'Little Miss' remains dome-shaped and compact throughout the growing season. The inventor also observed that 'Little Miss' exhibits strikingly colorful foliage from late spring and continuing into fall. Taking these characteristics together, the inventor determined that 'Little Miss' would be a useful and valuable addition to the available varieties of *Miscanthus* with particular applications for small gardens and in planted containers.

Asexual propagation of 'Little Miss' was first accomplished by the inventor in 2010 at the inventor's garden in Woellstein, Germany. The method of propagation used was division of the entire in-ground plant. Since that time under careful observation the inventor has determined that the characteristics of 'Little Miss' are fixed, uniform, and true to type in all subsequent generations of asexual propagation.

SUMMARY

The following traits have been repeatedly observed and represent the distinguishing characteristics of the new *Miscanthus* cultivar 'Little Miss'. These traits in combination set 'Little Miss' apart from all other existing varieties of *Miscanthus* known to the inventor. 'Little Miss' has not been tested under all possible conditions and phenotypic differences may be observed with variations in environmental, climatic and cultural conditions, however, without any variance in genotype.

1. 'Little Miss' exhibits a compact and mounding foliage habit in all stages of growth and when established in the garden and landscape.
2. After one year's growth in a container, 'Little Miss' is approximately 40 cm in height and 30 cm in diameter, excluding the height of the flowers.
3. Established and mature plants of 'Little Miss' achieve a height of 60 cm and a spread of 90 cm with flowers extending to 1 m above the base.
4. The first spring foliage growth of 'Little Miss' is green in color.
5. Depending on spring light conditions, the upper surfaces of the leaves of 'Little Miss' become red in color as early as April (in southern California) or May (in Germany).
6. As summer proceeds into fall, the foliage of 'Little Miss' becomes more increasingly deep burgundy red in color.
7. By fall, the foliage of 'Little Miss' is predominantly deep red in color.
8. 'Little Miss' blooms from July to October.
9. 'Little Miss' is hardy in USDA Zone 6.

BRIEF DESCRIPTION OF THE PHOTOGRAPHS

The accompanying color photographs illustrate the overall appearance of the new *Miscanthus* variety 'Little Miss' showing colors as true as it is reasonably possible to obtain in colored reproductions of this type. Colors in the photographs may differ from the color values cited in the detailed botanical description, which accurately describe the actual colors of the new variety 'Little Miss'.

Figure 1:
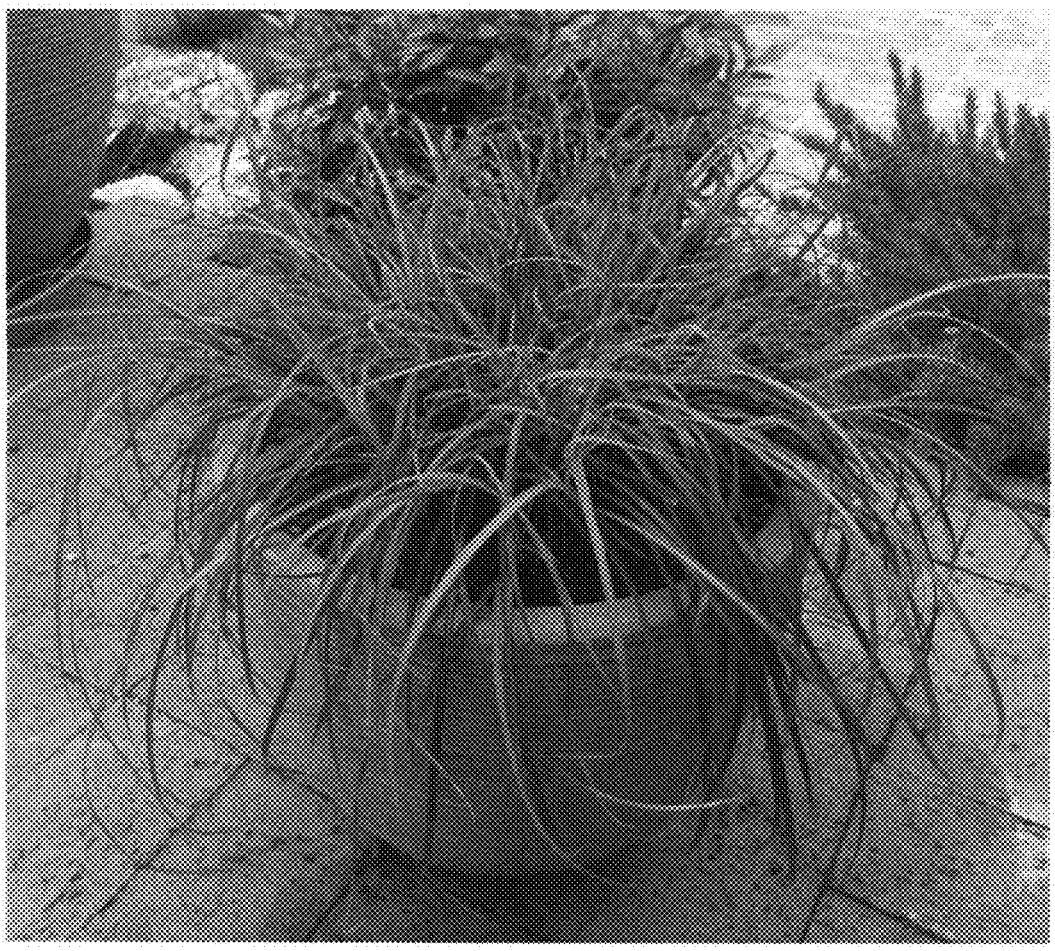
FIG. 1 depicts a two-year old plant of 'Little Miss' growing outdoors in Santa Barbara, Calif. This photograph was taken in April and depicts the early red coloration of the foliage.
Figure 2:
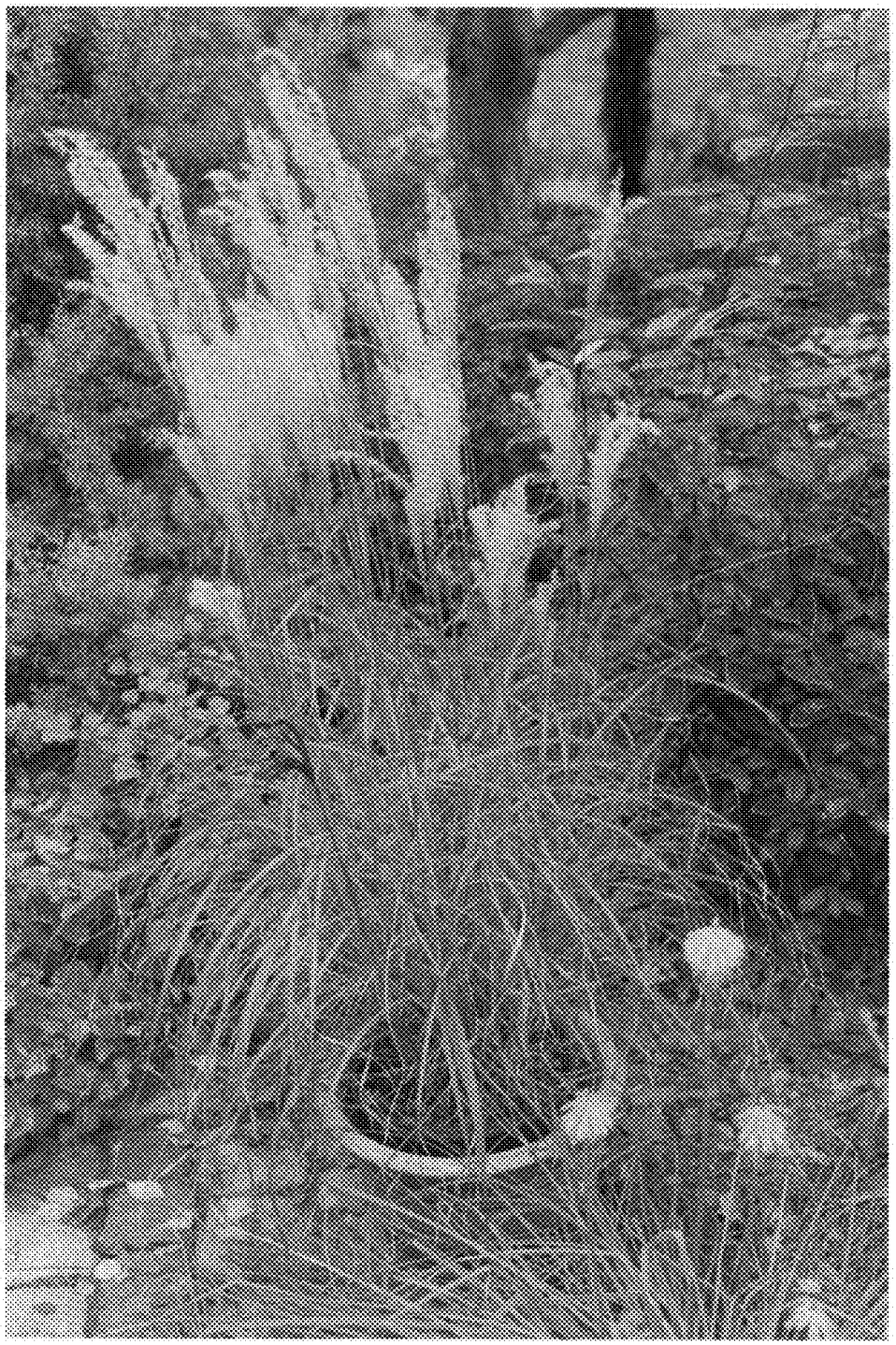
FIG. 2 depicts a two-year old plant of 'Little Miss' growing in a five liter container outdoors in the inventor's garden in Woellstein, Germany. This photograph was taken in late summer and depicts the inflorescence and red coloration of the foliage on a mature plant.
Figure 3:
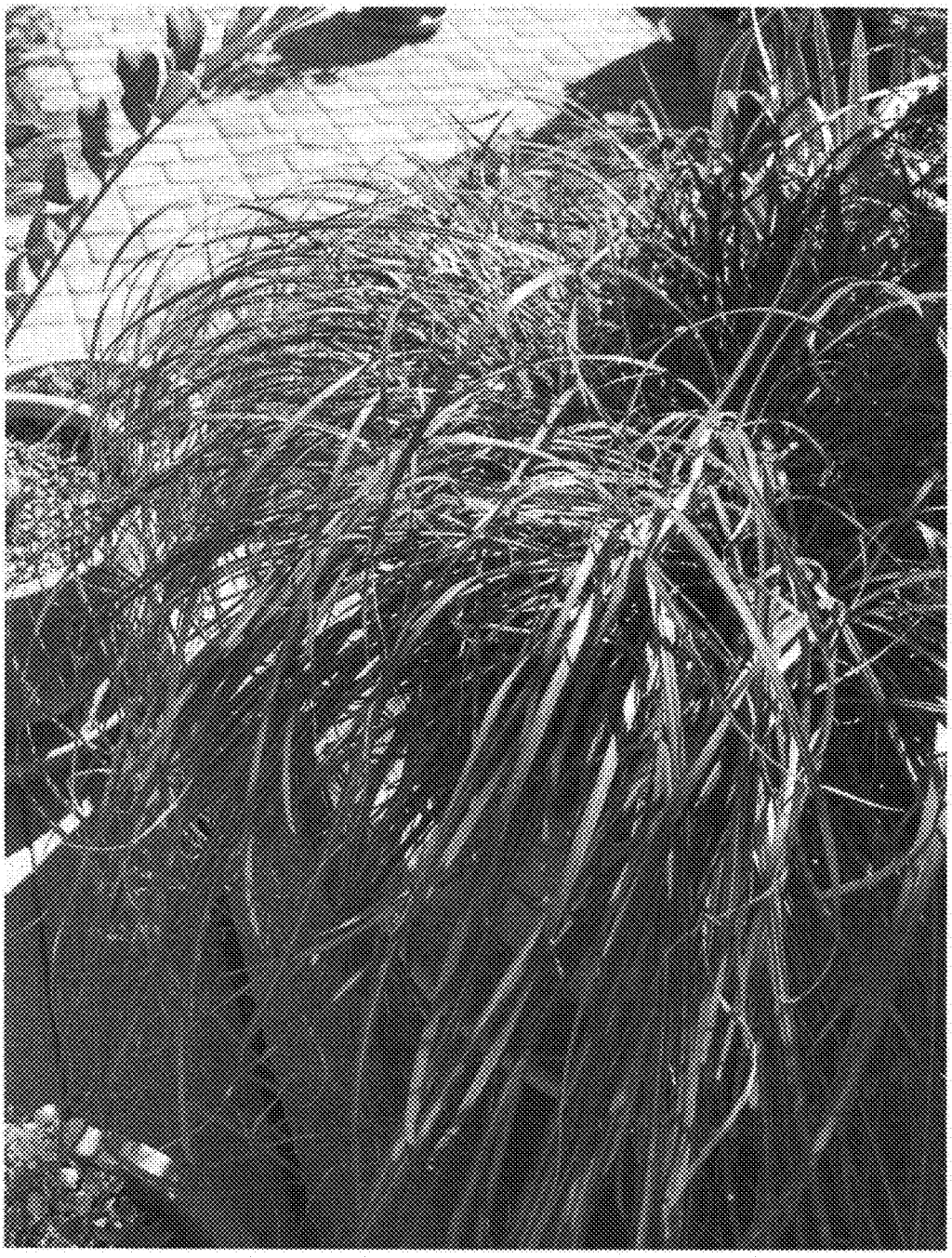
FIG. 3 depicts a two-year old plant of 'Little Miss' growing outdoors in Santa Barbara, Calif. This photograph was taken in November and depicts the deep red fall coloration of the foliage.

The photographs were made using conventional techniques and although flower and foliage color may appear different from actual color due to light reflectance, they are as accurate as possible by conventional photography.

BOTANICAL DESCRIPTION OF THE PLANT

The following is a detailed botanical description of 'Little Miss' which has been prepared from observations and measurements in 2015 and 2016 in Santa Barbara, Calif. from 9 to 15 month old plants growing outdoors in 2 and 3 gallon containers. Color determinations are made in accordance with the 2007 edition of The Royal Horticultural Society Colour Chart, London, England, except where general color terms of ordinary dictionary significance are used. The growing requirements of 'Little Miss' are similar to the species *Miscanthus sinensis.*

Botanical classification:

*Family*.—Poaceae.

*Genus.—Miscanthus.*

*Species.—sinensis.*

*Common name*.—Maiden Grass.

*Variety*.—'Little Miss'.

Parentage: 'Little Miss' was selected as an open pollinated seedling raised from unnamed seed of the species *Miscanthus sinensis.*

Plant description:

*Growth habit*.—Compact mounding.

*Commercial category*.—Ornamental grass.

*Use*.—For garden and landscape.

*Suitable container sizes.*—1 gallon container or larger.

*Propagation method*.—Division of established in-ground or container-grown plants or tissue culture.

*Rooting system*.—Fibrous.

*Crop time* (*range*).—9 to 12 months to produce a 1 gallon container from a plant division.

*Plant dimensions* (*first year*).—30 cm in height (excluding the flowers) and 40 cm in diameter.

*Plant dimensions* (*at maturity*).—60 cm in height (excluding the flowers) and 90 cm in width.

*Height in flower* (*including the flowers*).—60 cm in first year, up to 1 m when established and mature.

*Cultural requirements*.—Grow in full sun and well-draining porous soil, with moderate water.

*Hardiness*.—USDA Zone 6.

Culm (stem):

*Dimensions*.—Up to 25 cm in length and 3 mm in diameter.

*Shape*.—Cylindrical, hollow.

*Surface*.—Glabrous.

*Color*.—Emerges 143C, maturing to 146C.

*Node dimensions*.—3 mm in length, 2 mm in width.

*Internode distance*.—5 cm to 8 cm.

*Ligules*.—Membranaceous, approximately 4 mm in length; color (mid-summer) 153A; surface pubescent, hairs 2 mm to 3 mm in length, fine, color NN155C.

Foliage:

*Leaves quantity*.—Up to 10 leaves per culm.

*Leaf aspect*.—Initially upright then arching and fully reflexing.

*Attachment*.—Sheathing.

*Leaf shape*.—Concave, linear.

*Leaf dimensions* (*mid-summer*).—22 cm in length, 6 mm in width.

*Leaf margin*.—Microscopically serrulate, teeth angled towards apex.

*Leaf surface* (*both surfaces*).—Glabrous.

*Leaf color* (*emerging after winter dormancy, both surfaces*).—143C.

*Leaf color* (*late spring and summer*).—143C becoming 182A first on adaxial surface and then both surfaces.

*Leaf color* (*late summer and fall, both surfaces*).—Ranges between 53A and 187C. Very occasionally leaves remain green, 143C.

*Leaf apex*.—Acute.

*Leaf base*.—Truncate.

*Venation pattern*.—Parallel.

*Midrib* (*adaxial surface*).—Depressed.

*Midrib color* (*adaxial surface, after winter dormancy*).—144B.

*Midrib color* (*adaxial surface, late spring and summer*).—144B becoming 181C.

*Midrib color* (*adaxial surface, late summer and fall*).—53B becoming 182A.

*Midrib* (*abaxial surface*).—Prominent, raised.

*Midrib color* (*abaxial surface, after winter dormancy*).—same as leaf, 143C.

*Midrib color* (*abaxial surface, late spring and summer*).—same as leaf, 143C, becoming 182A.

*Midrib color* (*abaxial surface, late summer and fall*).—Same as leaf: ranges between 53A and 187C.

Inflorescence:

*Type*.—Terminal panicle, one panicle per culm.

*Panicle appearance*.—Plumose, consisting of numerous (approximately 25) silky racemes. Racemes consist of approximately 50 spikelets arranged in pairs.

*Panicle dimensions*.—Up to 15 cm in length, 10 cm in width.

*Raceme dimensions*.—8 cm to 10 cm in length, 3 cm in width.

*Panicle and raceme color*.—NN155C ageing to 161A.

*Spikelets*.—Up to 5 mm in length, 1 mm to 2 mm in width; fine white hairs colored RHSNN155C emerging from base; spikelet color NN155C.

*Pedicel*.—3 mm to 7 mm in length, 1 mm in diameter, color 166B.

*Lemma dimensions*.—3 mm in length, 1 mm in diameter, color 165C. Lemma base truncate, apex acute, margin entire, texture smooth.

*Palea dimensions.*—2.5 mm to 3 mm in length, 1 mm in diameter, color 165C. Palea base truncate, apex acute, margin entire, texture smooth.

*Awn.*—6 mm in length, 0.2 mm in diameter, color 165D.

*Bloom period.*—July to October.

*Persistent or self-cleaning.*—Persistent.

*Fragrance.*—None observed.

Reproductive organs:

*Stamens.*—3 in number, filaments 2 mm to 3 mm in length, 0.2 mm in diameter, color NN155C.

*Anthers.*—2 mm in length, less than 0.5 mm in width, color 200D.

*Pistil quantity.*—1.

*Stigma.*—2 in number, shape plumose, color 200A.

*Pollen.*—Not observed.

*Ovary.*—Superior, rounded, 1 mm in diameter.

Fruit and seed: None observed to date.

Diseases and pests: None known to the inventor.

COMPARISON KNOWN VARIETY

The parents of 'Little Miss' are unknown to the inventor and a comparison between 'Little Miss' and its parents is not possible. The inventor considers that two varieties of *Miscanthus* are close in some respects to 'Little Miss'. First, the variety 'Adagio' (unpatented) is considered to be compact in habit. However, 'Adagio' does not exhibit colorful foliage at any time of the year. Second, the selection of *Miscanthus purpurescens* (unpatented) is renowned for its purple foliage. However *Miscanthus purpurescens* grows to three times the height of 'Little Miss' and becomes loose and open as the season proceeds. In addition, *M. purpurescens* does not develop the striking red tones which are characteristic of 'Little Miss' in the fall.

I claim:

1. A new and distinct cultivar of *Miscanthus* plant named 'Little Miss' as described and illustrated herein.

* * * * *